US00PP35185P2

(12) United States Plant Patent
Koppe

(10) Patent No.: US PP35,185 P2
(45) Date of Patent: May 23, 2023

(54) ***BEGONIA* PLANT NAMED 'KRBEVRE01'**

(50) Latin Name: ***Begonia* x *hiemalis***
Varietal Denomination: KRBEVRE01

(71) Applicant: KOPPE ROYALTY B.V., Putten (NL)

(72) Inventor: Lubbertus H. Koppe, Putten (NL)

(73) Assignee: Koppe Royalty B.V., Putten (NL)

( * ) Notice: Subject to any disclaimer, the term of this patent is extended or adjusted under 35 U.S.C. 154(b) by 0 days.

(21) Appl. No.: 17/844,020

(22) Filed: Jun. 19, 2022

(51) Int. Cl.
*A01H 5/02* (2018.01)
*A01H 6/18* (2018.01)

(52) U.S. Cl.
USPC ..... Plt./349

(58) Field of Classification Search
USPC ..... Plt./349
CPC ... A01H 5/02; A01H 5/00; A01H 6/18; A01H 6/185
See application file for complete search history.

(56) References Cited

U.S. PATENT DOCUMENTS

PP30,440 P2 * 4/2019 Koppe ..... A01H 6/185 Plt./349

OTHER PUBLICATIONS

Koppe Begonia 2021-2022, retrieved on Aug. 25, 2022 at http://flora-land.ro/floraland/wp-content/uploads/2021/07/Koppe-catalogus-2021-2022.pdf, pp. 1-5, 10-13. (Year: 2022).*
BFG Supply Plantpeddler 2021-2022 Program, retrieved on Aug. 25, 2022 at https://bfgsupply.com/media/4339/2021-2022-plantpeddler-product-program.pdf, 4 pp. (Year: 2022).*

* cited by examiner

*Primary Examiner* — June Hwu
(74) *Attorney, Agent, or Firm* — C. Anne Whealy

(57) ABSTRACT

A new and distinct cultivar of *Begonia* plant named 'KRBEVRE01' characterized by its relatively compact, broadly upright and mounded plant habit; moderately vigorous growth habit and moderate growth rate; moderately freely branching habit; dark green-colored leaves; freely flowering habit; double-type male flowers that are red in color and held above and beyond the foliar plane; and good postproduction longevity.

2 Drawing Sheets

Figure 1:
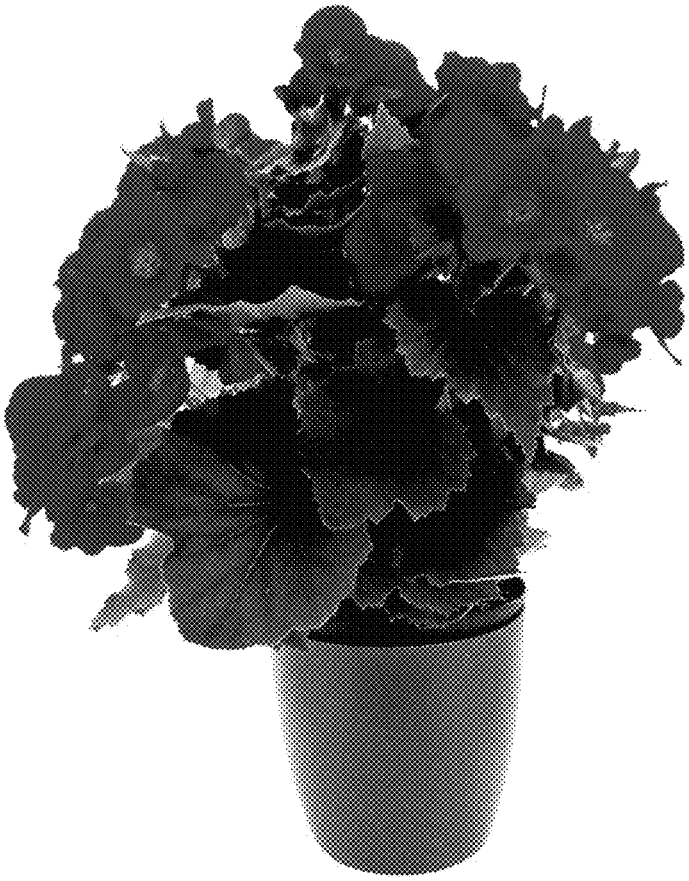

Botanical designation: *Begonia* x *hiemalis*.
Cultivar denomination: 'KRBEVRE01'.

STATEMENT REGARDING PRIOR DISCLOSURES BY THE INVENTOR/APPLICANT & ASSIGNEE

An European Community Plant Breeder's Rights application for the instant plant was filed by the Applicant/Assignee, Koppe Royalty B.V. of Putten, The Netherlands on Nov. 3, 2020, application number 2020/2760. Foreign priority is not claimed to this application.

The Inventor and Applicant/Assignee assert that no publications nor advertisements relating to sales, offers for sale or public distribution occurred more than one year prior to the effective filing date of this application. Any information about the claimed plant would have been obtained from a direct or indirect disclosure from the Inventor and/or Applicant/Assignee. Inventor and Applicant/Assignee claim a prior art exception under 35 U.S.C. 102(b)(1) for disclosure and/or sales prior to the filing date but less than one year prior to the effective filing date.

BACKGROUND OF THE INVENTION

The present invention relates to a new and distinct cultivar of *Begonia* plant, botanically known as *Begonia* x *hiemahs*, commercially referred to as an Elatior *Begonia* and hereinafter referred to by the name 'KRBEVRE01'.

The new *Begonia* plant is a product of a planned breeding program conducted by the Inventor in Ermelo, The Netherlands. The objective of the breeding program is to create new freely-branching *Begonia* plants with excellent postproduction longevity and attractive flower color.

The new *Begonia* plant originated from a cross-pollination made by the Inventor in February, 2016 of a proprietary selection of *Begonia* x *tuberhybrida* identified as code number KV13K1903-013, not patented, as the female, or seed, parent with a proprietary selection of *Begonia socotrana* identified as code number S00, not patented, as the male, or pollen, parent. The new *Begonia* plant was discovered and selected by the Inventor as a single flowering plant from within the progeny of the stated cross-pollination in a controlled greenhouse environment in Ermelo, The Netherlands in January, 2017.

Asexual reproduction of the new *Begonia* plant by terminal vegetative cuttings taken in a controlled greenhouse environment in Ermelo, The Netherlands since March, 2017 has shown that the unique features of this new *Begonia* plant are stable and reproduced true to type in successive generations.

SUMMARY OF THE INVENTION

Plants of the new *Begonia* have not been observed under all possible combinations of environmental conditions and cultural practices. The phenotype may vary somewhat with variations in environmental conditions such as temperature, daylength and light intensity, without, however, any variance in genotype.

The following traits have been repeatedly observed and are determined to be the unique characteristics of 'KRBEVRE01'. These characteristics in combination distinguish 'KRBEVRE01' as a new and distinct *Begonia* plant:

1. Relatively compact, broadly upright and mounded plant habit.
2. Moderately vigorous growth habit and moderate growth rate.
3. Moderately freely branching habit.
4. Dark green-colored leaves.
5. Freely flowering habit.
6. Double-type male flowers that are red in color and held above and beyond the foliar plane.
7. Good postproduction longevity.

Plants of the new *Begonia* differ primarily from plants of the female parent selection in the following characteristics:

1. Plants of the new *Begonia* have smaller leaves than plants of the female parent selection.
2. Plants of the new *Begonia* have red-colored flowers whereas plants of the female parent selection have orange-colored flowers.

Plants of the new *Begonia* differ primarily from plants of the male parent selection in the following characteristics:

1. Plants of the new *Begonia* have larger flowers than plants of the male parent selection.
2. Plants of the new *Begonia* have red-colored flowers whereas plants of the male parent selection have purplish pink-colored flowers.

Plants of the new *Begonia* can be compared to plants of *Begonia* x *hiemalis* 'KRBEVCH01', disclosed in U.S. Plant Pat. No. 30,440. In side-by-side comparisons conducted in Ermelo, The Netherlands, plants of the new *Begonia* differ primarily from plants of 'KRBEVCH01' in flower color as flowers of plants of the new *Begonia* are more red and not as purplish red as flowers of plants of 'KRBEVCH01'.

BRIEF DESCRIPTION OF THE PHOTOGRAPHS

The accompanying colored photographs illustrate the overall appearance of the new *Begonia* plant showing the colors as true as it is reasonably possible to obtain in colored reproductions of this type. Colors in the photographs may differ slightly from the color values cited in the detailed botanical description which accurately describe the colors of the new *Begonia* plant.

The photograph on the first sheet (FIG. 1) comprises a side perspective view of a typical plant of 'KRBEVRE01' grown in a container.

Figure 2:
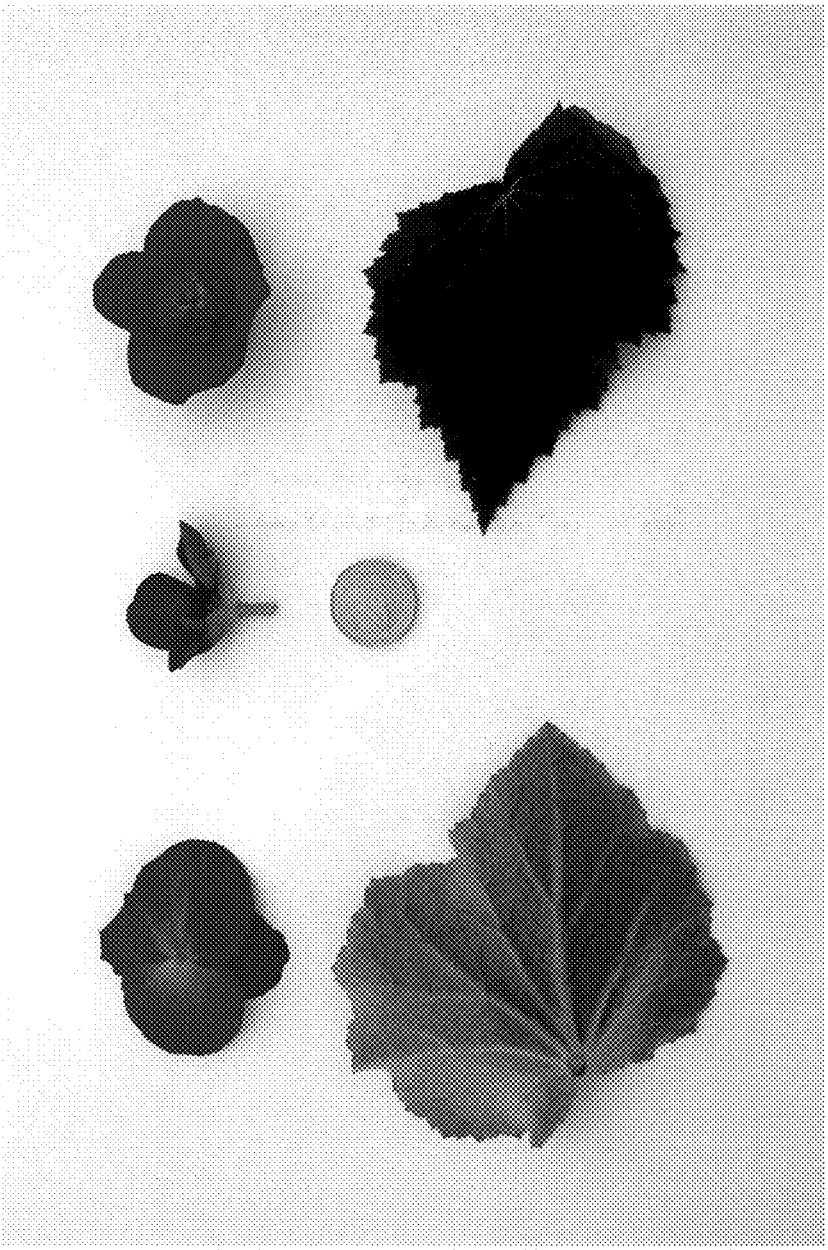

The photograph on the second sheet (FIG. 2) are close up views of the upper (right) and lower (left) surfaces of typical leaves and flowers of 'KRBEVRE01', and in the center of the photograph is a close-up view of a typical flower bud.

DETAILED BOTANICAL DESCRIPTION

The aforementioned photographs and following observations and measurements describe plants grown during the early summer in 13-cm containers in a glass-covered greenhouse in Ermelo, The Netherlands and under cultural practices typical of commercial *Begonia* production. During the production of the plants, day temperatures ranged from 20° C. to 22° C. and night temperatures ranged from 16° C. to 18° C. Plants were eleven weeks old when the photographs and description were taken. In the following description, color references are made to The Royal Horticultural Society Colour Chart, 2015 Edition, except where general terms of ordinary dictionary significance are used.

Botanical classification: *Begonia* x *hiemalis* 'KRBEVRE01'.

Parentage:

*Female, or seed, parent.*—Proprietary selection of *Begonia* x *tuberhybrida* identified as code number KV13K1903-013, not patented.

*Male, or pollen, parent.*—Proprietary selection of *Begonia socotrana* identified as code number S00, not patented.

Propagation:

*Type.*—By terminal vegetative cuttings.

*Time to initiate roots, summer and winter.*—About 20 days at temperatures about 20° C.

*Time to produce a rooted young plant, summer and winter.*—About five weeks at temperatures about 20° C.

*Root description.*—Fine, fibrous; typically white to orangish brown in color, actual color of the roots is dependent on substrate composition, water quality, fertilizer type and formulation, substrate temperature and physiological age of roots.

*Rooting habit.*—Freely branching; medium density; plants of the new *Begonia* have not been observed to form tubers.

Plant description:

*Plant habit and form.*—Relatively compact, broadly upright and mounded plant habit; overall plant shape, obovate.

*Growth habit.*—Moderately vigorous growth habit and moderate growth rate; suitable for 9-cm and larger containers; under optimal environmental and cultural conditions, usually about nine weeks from rooted cuttings are required to produce proportional plants in 13-cm containers.

*Branching habit.*—Moderately freely branching with about four primary branches each with about three secondary branches developing per plant.

*Plant height, soil level to top of foliar plane.*—About 25.9 cm.

*Plant height, soil level to top of floral plane.*—About 29 cm.

*Plant width.*—About 36.7 cm.

*Lateral branches.*—Length: About 9.6 cm. Diameter: About 8 mm to 9 mm. Internode length: About 2.9 cm. Strength: Moderately strong. Aspect: Erect to about 50° from vertical. Texture and luster: Sparsely pubescent; slightly glossy. Color, developing and fully developed: Close to 146B. Lenticels: None observed on plants of the new *Begonia* to date.

*Leaves.*—Arrangement: Alternate, simple. Length: About 13.3 cm. Width: About 10.6 cm. Shape: Broadly ovate. Apex: Acute. Base: Oblique, lobes free and not imbricate. Margin: Serrate to dentate; slightly to moderately undulate. Texture and luster, upper surface: Mostly smooth, glabrous with sparse pubescence along the veins; velvety; glossy. Texture and luster, lower surface: Mostly smooth, glabrous with sparse pubescence along the veins; velvety; glossy. Venation pattern: Pinnate. Color: Developing leaves, upper surface: Close to a blend of 137A and NN137A; narrow edges, close to 183D. Developing leaves, lower surface: Close to 148B; narrow edges, close to 183D. Fully expanded leaves, upper surface: Darker than a blend of 139A and 147A; venation, close to 143A. Fully expanded leaves, lower surface: Close to 191A; venation, close to 146B. Petioles: Length: About 5.2 cm. Diameter: About 5 mm. Strength: Low, flexible. Texture and luster, upper and lower surfaces: Sparsely pubescent; slightly glossy. Color, upper surface: Close to a blend of 152A and 199A; distally, strongly tinged with close to 185A. Color, lower surface: Close to 152B. Stipules: Quantity and appearance: Two leafy stipules at the base of each leaf. Length: About 1.2 cm. Width: About 1.1 cm. Shape: Broadly ovate. Apex: Obtuse. Base: Broadly cuneate. Margin: Ciliate. Color, upper and lower surfaces: Close to 144A; margins, close to 182D.

Flower description:

*Flower form and flowering habit.*—Fully double-type male rotate flowers arranged in axillary cymes; to date, female flower development has not been observed on plants of the new *Begonia*; typically about five flowers per cyme, numerous cymes in flower simultaneously and about 320 flowers developing per plant; flowers face upright to outwardly and are positioned above and beyond the foliar plane.

*Natural flowering season.*—Plants flower continuously from the spring into the autumn in The Netherlands.

*Flower longevity.*—Individual flowers last about ten days on the plant; flowers not persistent.

*Fragrance.*—None detected.

*Inflorescence height.*—About 14.6 cm.

*Inflorescence diameter.*—About 11 cm.

*Flower buds.*—Length: About 2.2 cm. Diameter: Ranging from about 0.8 cm to 2.2 cm. Shape: Broadly obovate to roughly circular, flattened. Texture and luster: Smooth, glabrous; velvety; matte. Color: Close to 45C; towards the margins, close to 45A and towards the base, close to 45D.

*Male flowers.*—Diameter: About 5.5 cm by 6.1 cm. Depth: About 2.8 cm. Tepals: Quantity and arrangement: About four arranged in two whorls. Length, inner whorl tepals: About 2.7 cm. Length, outer whorl tepals: About 3.6 cm. Width, inner whorl tepals: About 2.9 cm. Width, outer whorl tepals: About 3.8 cm. Shape: Roughly orbicular to reniform. Apex: Mostly rounded. Base, inner whorl tepals: Cuneate. Base, outer whorl tepals: Truncate. Margin: Entire, not undulate. Texture and luster, upper surface: Smooth, glabrous; velvety; not rugose; matte. Texture and luster, lower surface: Smooth, glabrous; moderately velvety; not rugose; matte. Color, inner whorl tepals: When opening, upper surface: Close to 45B. When opening, lower surface: Close to 45B; towards the base, close to 43A. Fully opened, upper surface: Close to 45B; towards the base, close to 44B; venation, close to 45B; color does not change with subsequent development. Fully opened, lower surface: Close to 42A; towards the base, close to 45D; venation, close to 46A; color does not change with subsequent development. Color, outer whorl tepals: When opening, upper surface: Close to 45B. When opening, lower surface: Close to 45B; towards the base, close to 43A. Fully opened, upper surface: Close to 45B; towards the base, close to 43A; venation, close to 45B; color does not change with subsequent development. Fully opened, lower surface: Close to 42A; venation, close to 46A; color does not change with subsequent development. Tepaloids: Quantity and arrangement per flower: Variable, about 55 per flower arranged in about five whorls. Length: About 0.9 cm to 1.3 cm. Width: About 0.8 cm to 1.1 cm. Shape: Obovate to broadly oblong or orbicular. Apex: Praemorse to obtuse. Base: Broadly acute. Margin: Entire to irregularly crenate; not undulate. Texture and luster, upper and lower surfaces: Smooth, glabrous; velvety; not rugose; matte. Color: When opening, upper surface: Close to 17C; towards the margins, close to 28B. When opening, lower surface: Close to 17C. Fully opened, upper surface: Close to 21A strongly flushed and mottled with close to 30A, 30B and 45B; venation, similar to lamina color; color does not change with subsequent development. Fully opened, lower surface: Close to 24A strongly flushed and mottled with close to 24B, 24C, 30D, 43A, 44A and 44B; venation, similar to lamina color; color does not change with subsequent development.

*Flower bracts.*—Quantity and arrangement: Two positioned at the top of the peduncle. Length: About 1.8 cm. Width: About 2 cm. Shape: Reniform. Apex: Obtuse to broadly and shallowly praemorse. Base: Broadly cuneate. Margin: Ciliate. Texture and luster, upper and lower surfaces: Smooth, glabrous; moderately velvety; slightly glossy. Color, upper surface: Close to 46A, 180A and 185A flushed and marbled with close to 145A and 146C to 146D. Color, lower surface: Close to 180A, 181A and 185A flushed and marbled with close to 146C to 146D.

*Peduncles.*—Length: About 6.9 cm. Diameter: About 4 mm. Strength: Moderately strong. Aspect: About 45° from lateral branch axis. Texture and luster: Smooth, glabrous; moderately glossy. Color: Close to 152B; distally, tinged with close to 175A.

*Pedicels.*—Length: About 2.1 cm. Diameter: About 2 mm. Strength: Moderately strong. Aspect: About 45° from peduncle axis. Texture and luster: Moderately pubescent; moderately glossy. Color: Close to N34D and N170A.

*Reproductive organs.*—To date, stamen and pistil development have not been observed on plants of the new *Begonia*.

*Seeds and fruits.*—To date, seed and fruit development have not been observed on plants of the new *Begonia*.

Pathogen & pest resistance: To date, resistance to pathogens and pests common to *Begonia* plants has not been observed on plants of the new *Begonia*.

Temperature tolerance: Plants of the new *Begonia* have been observed to tolerate high temperatures about 35° C. and to be suitable for USDA Hardiness Zones 10 to 12.

It is claimed:

1. A new and distinct *Begonia* plant named 'KRBEVRE01' as illustrated and described.

* * * * *